United States Patent [19]

Kesling

[11] 4,026,021
[45] May 31, 1977

[54] HOLDER FOR ORTHODONTIC TYING ATTACHMENT

[76] Inventor: Peter C. Kesling, Green Acres, LaPorte, Ind. 46350

[22] Filed: Nov. 3, 1975

[21] Appl. No.: 628,508

[52] U.S. Cl. .............................................. 32/14 A
[51] Int. Cl.² ....................................... A61C 13/00
[58] Field of Search ............... 32/14 A, 14 R, 14 E, 32/1; 206/329, 476, 485, 486, 526, 578, 531, 532, 348

[56] References Cited
UNITED STATES PATENTS

| | | | |
|---|---|---|---|
| 1,378,262 | 5/1921 | Meyer | 206/486 |
| 1,445,795 | 2/1923 | Parker | 206/486 X |

*Primary Examiner*—Robert Peshock
*Attorney, Agent, or Firm*—Lockwood, Dewey, Zickert & Alex

[57] ABSTRACT

A holder for an orthodontic tying attachment that is disc-shaped and which holder includes a pair of panels joined at one edge between which the attachment is placed and in alignment with a opening in the panels at the joined edge through which the attachment may be forced when removing the attachment from the holder. A plurality of attachments may be carried by the holder which facilitates the mounting of attachments onto bands.

6 Claims, 14 Drawing Figures

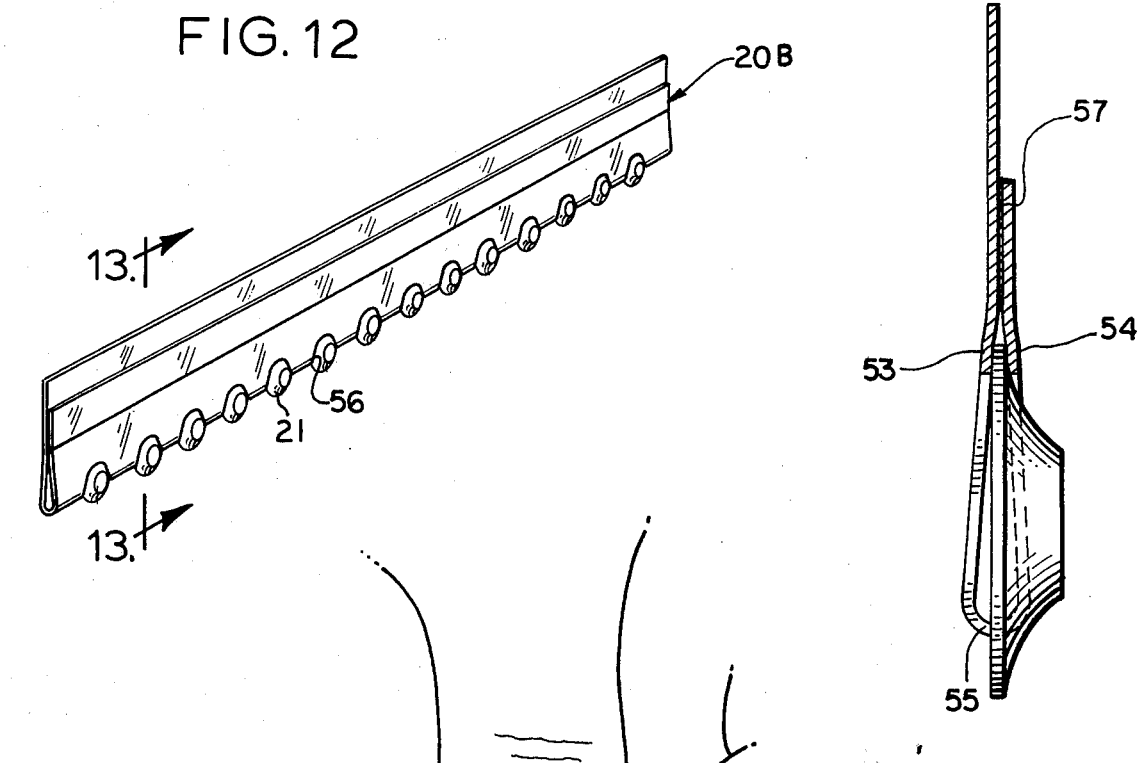
FIG.12
FIG.13
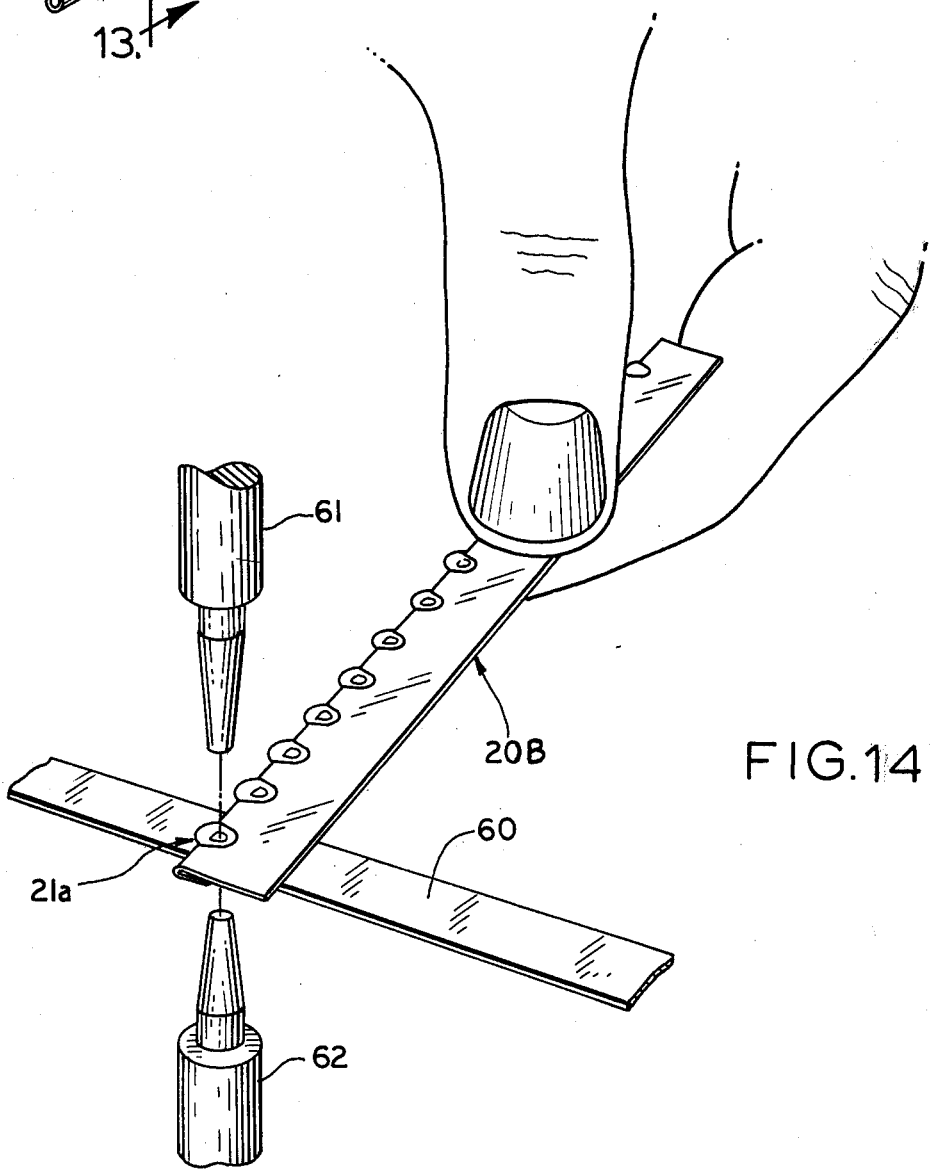
FIG.14

HOLDER FOR ORTHODONTIC TYING ATTACHMENT

This invention relates in general to orthodontic appliances, and more particularly to a holder for one or more orthodontic appliances to facilitate the mounting of appliances onto bands, and still more particularly to a holder for orthodontic tying attachments generally circular in shape.

Orthodontic appliances such as brackets, buttons, tubes and the like, are generally mounted on the teeth of a patient by first attaching the appliance to a band and then cementing the band and appliance in place on a tooth. In some instances, the appliances may be secured directly to the tooth. These appliances are extremely small in size and handling requires considerable patience and dexterity. Where the appliances are mounted onto bands, they may be inadvertently dropped and lost. If a sufficient number of appliances is lost, such can be costly. Further, locating a dropped appliance can lead to lost time. It has been heretofore proposed to use a holder for brackets as in U.S. Pat. No. 3,657,817.

The holder of the present invention is primarily concerned with the handling of orthodontic tying attachments such as disclosed in my copending patent application Ser. No. 457,465, filed Apr. 3, 1974, although it may be appreciated the holder of the present invention may be utilized efficiently with other types of appliances. Further, the holder of the present invention facilitates the packaging of a plurality of orthodontic appliances during the marketing of appliances.

The holder of the invention is preferably constructed of a relatively stiff transparent acetate, although any suitable plastic or paper material may be employed. Further, the material may be translucent or opaque if desired. It can be appreciated that transparency of the holder facilitates the mounting of the appliance onto a band. The holder includes a pair of juxtaposed panels folded together along a fold line which is also provided with openings through which a part of the appliance will be exposed when the appliance is locked into place on the holder. The opening at the fold line is slightly narrower than the dimension of the appliance at the opening. For example, if the appliance is circular, the diameter of the appliance would be slightly larger than the width of the opening at the fold line. One end of the holder can be grasped by the fingers of appliance person during alignment of an ppliance onto a tooth band and during fastening of the appliance on the tooth band, such as by welding or soldering or the like. Once the appliance is secured to the tooth band, it may be separated from the holder by pulling the appliance through the opening which will expand or enlarge by virtue of the material of the holder and thereby separate the holder and appliance.

It is therefore an object of the present invention to provide a new and improved holder for orthodontic appliances to facilitate the packaging of the appliances and the mounting of the appliances onto bands.

A further object of this invention is in the provision of a new and improved holder for orthodontic appliances, such as orthodontic tying attachments, which may be inexpensively manufactured and filled with appliances to facilitate the mounting of the attachments onto bands.

Other objects, features and advantages of the invention will be apparent from the following detailed disclosure, taken in conjunction with the accompanying sheets of drawings, wherein like reference numerals refer to like parts, in which:

FIG. 12 is a perspective view of a still further modified holder according to the invention;

FIG. 13 is an enlarged vertical sectional view taken substantially along line 13—13 of FIG. 12; and FIG. 14 is a perspective view illustrating the use of the holder in orienting an attachment onto a tooth band for the purpose of securing the attachment to the tooth band.

Figure 1:
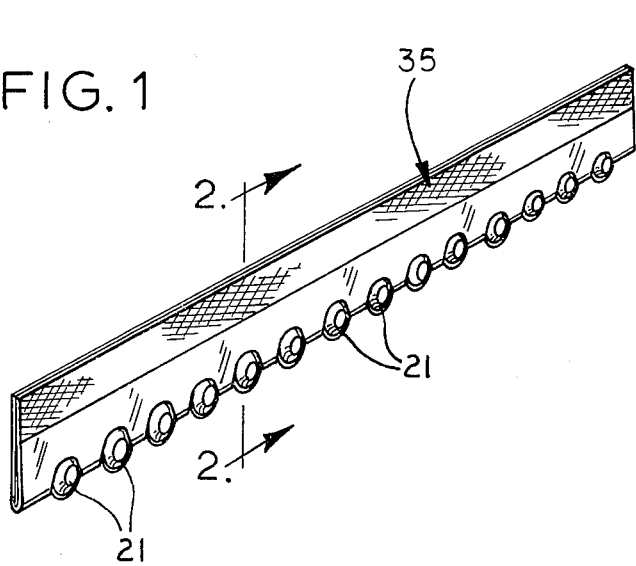
FIG. 1 is a perspective view of a holder according to the present invention and showing orthodontic appliances carried by the holder.
Figure 3:
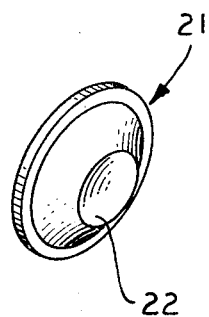
FIG. 3 is a perspective view of an orthodontic tying attachment that may be mounted in the holder of the present invention.

Referring now to the drawings, and particularly to the embodiment disclosed in FIGS. 1 to 7, a holder 20 according to the present invention is particularly illustrated in FIG. 1 with a plurality of orthodontic tying attachments 21 held in place. Thus, it can be appreciated that the holder 20 performs a packaging function in maintaining a plurality of attachments together for distribution purposes. It should be further appreciated that the holder is especially useful when it is desired to secure an attachment to a tooth band such as illustrated in FIG. 14.

The attachment 21 herein illustrated is disc-shaped or circular in shape and includes a protruding centrally disposed portion 22. The attachment illustrated is like that in my copending application Ser. No. 457,465, filed Apr. 3, 1974, although it should be appreciated that the holder herein disclosed may be suitable for use with other types of orthodontic appliances or attachments, especially where the appliances are to be secured to tooth bands.

Figure 6:
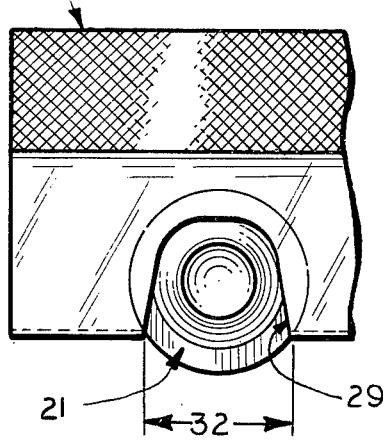
FIG. 6 is an enlarged front elevational view, partially fragmentary of the holder shown in FIG. 1 to illustrate the general dimensions of the attachment relative to the opening in the holder.

The holder 20 includes a pair of juxtaposed panels 26 and 27 folded together and interconnected at the fold line 28. An opening 29 is provided in the panels 26 and 27 through the fold line, and as seen particularly in FIG. 4, includes a cutout 30 in panel 26 and a cutout 31 in panel 27. The cutouts are essentially identical and sized so that the width of the opening 29 at the fold line, as indicated at 32 in FIG. 6, is slightly less than the diameter of the attachment 21. Accordingly, when an attachment is inserted between the panels and in alignment with the opening, as shown particularly in FIG. 6, the attachment cannot pass through the opening 29 and will therefore be retained by the holder. It should be further appreciated the opening exposes nearly all of the attachment and particularly the central area of the attachment which is the portion of the attachment to be secured onto a tooth band. Thus, it is important the cutouts be sized to expose that portion of the appliance on both sides to facilitate securing, and particularly welding the attachment to the band.

Figure 4:
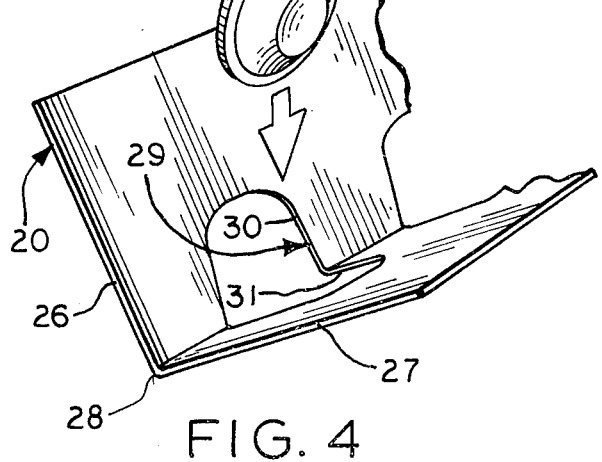
FIG. 4 is a perspective view illustrating the first step in assembling an attachment with the holder according to the present invention.
Figure 5:
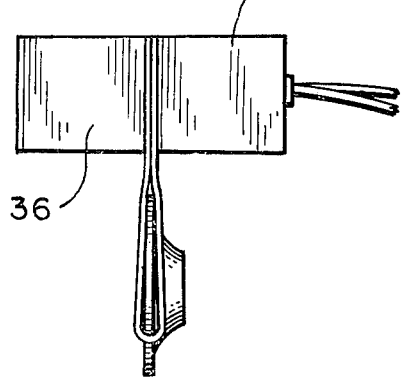
FIG. 5 is a side elevational view of the holder of the invention and illustrating the heat sealing of the two panels together at their free edges.

The free edges of the panels 26 and 27 may be secured together in any desirable fashion. Where the material is heat-sealable, as illustrated in the embodiment of FIGS. 1 to 7, the free edges of the panels away from the attachments may be heat-sealed together to define a heat-sealed joint 35 by use of any suitable heat-sealing device, as illustrated in FIG. 5, which includes a backing member 36 and a heated sealing bar 37. Other manners of securing the free edges of the panels together are illustrated in the embodiments of FIGS. 8 to 11 and 12 to 14. It should also be appreciated that the free edges may not need to be secured together if the material used for the holder is of such rigidity to maintain the edges together under normal conditions.

The material used for the panels of the holder is preferably of a stiffness to enhance the retainment of the attachments between the panels and prevent them from freely moving through the openings. Preferably, the holder is made of a transparent acetate of a suitable stiffness, such as that used in name card holders and the like. However, any suitable plastic or paper may be used. While it is preferred that the material utilized be transparent or clear so as to facilitate the mounting of attachments onto a tooth band, it should be appreciated that they could be opaque or translucent if desired. Further, if the holder were injection molded of a suitable plastic, it can be appreciated that it can be of a stiffness such that there would be no need to secure the free edges together as they would be biased together by the strength of the material. Accordingly, the material should be of a relatively stiff material so long as the attachments are properly held in the holder during normal handling.

Figure 7:
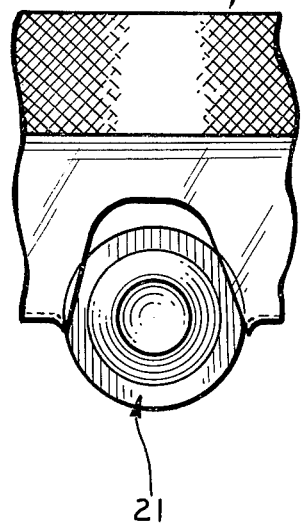
FIG. 7 is a view similar to FIG. 6 but illustrating the separation of the attachment from the holder where the areas of the holder at the opening are shown to expand allowing the holder to be pulled through the opening.
Figure 2:
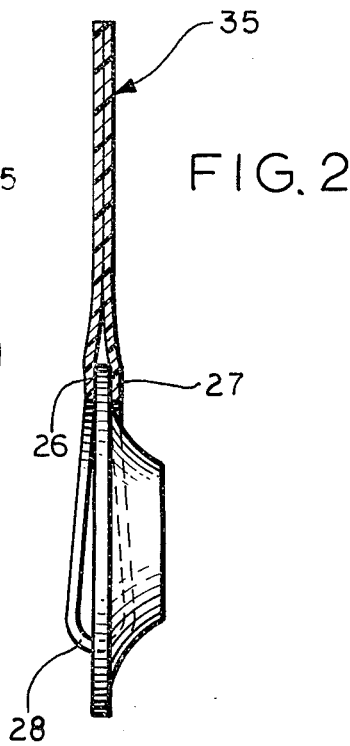
FIG. 2 is a greatly enlarged transverse sectional view taken substantially along line 2—2 of FIG. 1 and showing the attachment in side elevation.

When it is desired to remove an attachment from the holder, this can be accomplished by pulling the attachment through the opening 29 which enlarges or expands the width 32, as shown in FIG. 7, such that the attachment may be easily removed from the holder. Here it will be appreciated the material of the holder will provide some resistance to removal of an attachment. An attachment may be removed by grasping it with a suitable instrument, or it may be removed by first attaching it to a tooth band and then separating the holder from the attachment. The tying attachment illustrated is of a type that is normally welded to a tooth band in a manner shown in FIG. 14, wherein it can be appreciated a person can spot the attachment onto the band by grasping one end of the holder and maintaining it in position during the welding operation. Thereafter, as above indicated, the holder can be separated from the attachment. It can be appreciated here that the holder will therefore maintain the attachment readily accessible until it is to be used, thereby reducing the possibility of inadvertently dropping or losing the attachment.

The holder 20 can be easily made and thereafter easily filled or loaded with attachments. For example, the holder, if made of a transparent acetate, could be made from a sheet of acetate where the panels would be laid flat and the openings would be punched through the sheet. Thereafter, the panels could be folded together and the holder could be transferred to a station for loading with attachments. With the panels separated, as shown in FIG. 4, attachments can then be loaded into the openings. Thereafter, the panels may be closed together sandwiching the attachments in alignment with the openings and the free edges may be heat-sealed to complete the packaging of the attachments. As noted particularly in FIG. 2, the protruding central portion 22 of the attachments will protrude from the holder, and it is this portion that aligns with the opening and prevents shifting of the attachment in the holder. Therefore, the holder can be easily made and easily loaded with attachments for ultimate use by the orthodontist.

Figure 8:
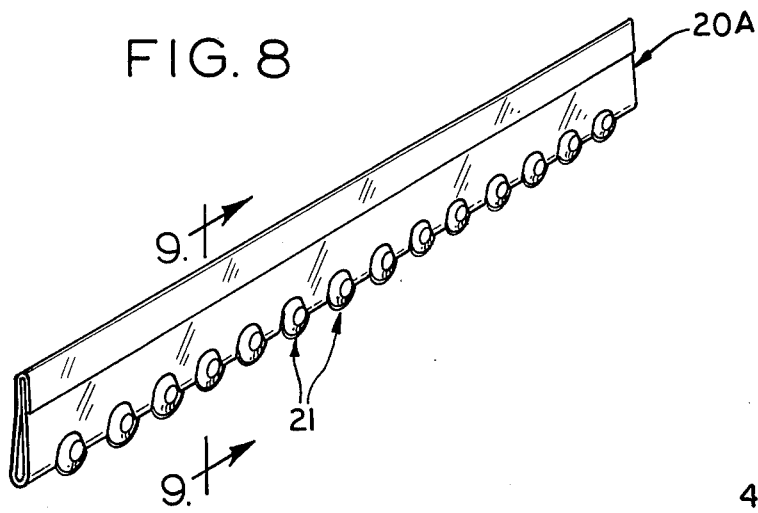
FIG. 8 is a perspective view of the modified holder according to the invention.
Figure 9:
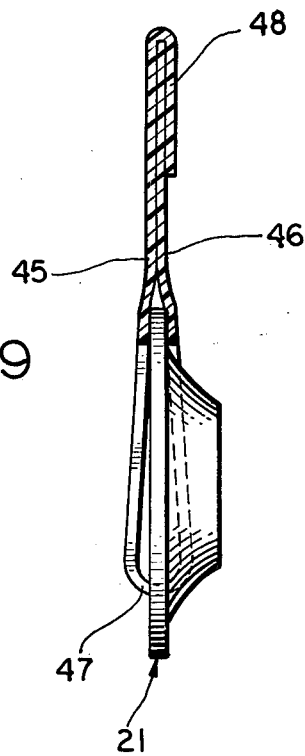
FIG. 9 is an enlrged vertical sectional view taken substantially along line 9—9 of FIG. 8.

The holder 20A shown in FIGS. 8 to 11 differs from the holder 20 only in the manner in which the free edges are attached or secured together. Holder 20A includes panels 45 and 46 folded together and interconnected by a fold line 47. At the free edge of panel 45, a locking flap 48 is attached which, as shown in FIGS. 8 and 9, overlies the free edge of panel 46 to lock the panels 45 and 46 together. Accordingly, it is not necessary to heat-seal the free edges of these panels together as with holder 20 as the locking flap 48 which is integral with the panel 45 is capable of maintaining the panels 45 and 46 tightly together to hold the attachments 21 in place in the openings 49. It can be appreciated that the holder could be made with any number of openings to retain any number of attachments.

Figure 10:
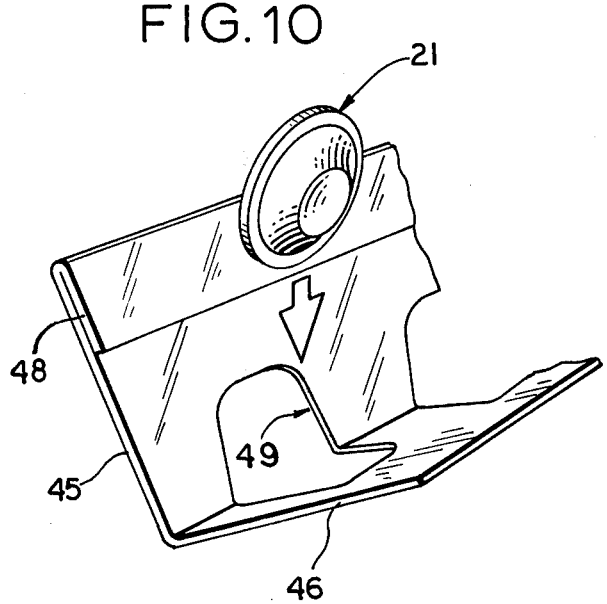
FIGS. 10 and 11 are large perspective views showing the steps of assembling attachments with the holder shown in FIGS. 8 and 9.
Figure 11:
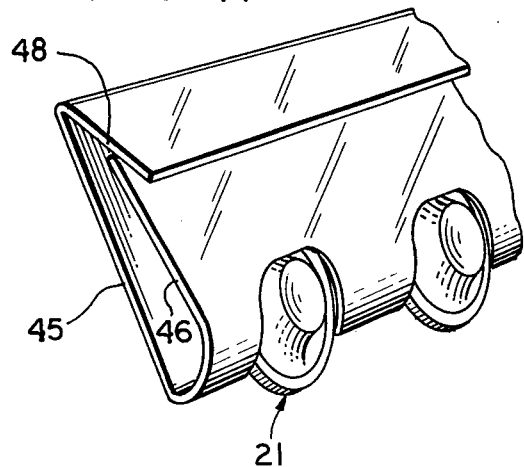

When assembling the attachments and holder 20A, the panels 45 and 46 are separated, as shown in FIG. 10, so that the attachments 21 can be inserted between the panels and in alignment with the openings 49. Thereafter, the locking flap 48 may be lifted, as shown in FIG. 11, to allow the free edge of the panel 46 to be inserted thereunder and ultimately complete the assembly of the attachments with the holder, as shown in FIG. 8 and 9.

A holder 20B forming another modification of the invention is illustrated in FIGS. 12 and 13 and includes juxtaposed panels 53 and 54 interconnected at a fold line 55 and provided with openings 56 for receiving the attachments 21 in the same manner as in the previous embodiments. This embodiment differs from the other embodiments in the manner in which the free edges of the panels are secured together. Particularly, the panel 54 is somewhat shorter or narrower than panel 53 and an adhesive 57 is provided between the panels 53 and 54 adjacent their free edges to secure the free edges together. The adhesive may be of any suitable type, such as a pressure sensitive adhesive, wherein the coating of the adhesive may be applied to one or ther other of the panels 53 and 54 and where mere pressure of the panels toward each other causes the adhesive to activate and secure the free edges together. While panel 54 is shown to be shorter than panel 53, it could be appreciated that they might be of the same size as desired, although such is not necessary.

The materials used for making the holders 20A and 20B are the same as that intended for the holder 20, and as understood from the foregoing, the only differences between the embodiments is in the manner in which the free edges are secured together.

Although heretofore referred to, the manner in which the attachments may be separated from the holder can be clearly appreciated from the illustration in FIG. 14, wherein the holder is grasped at one end by the hand of the operator to spot the attachment 21a onto a tooth band 60, all of which is positioned between welding electrodes 61 and 62 so that welding operations can be performed to secure the attachment to the band. Thereafter, the application of sufficient force to the holder will separate it from the attachment on the band and the next attachment may then be suitably secured to a band.

It will be understood that modifications and variations may be effected without departing from the scope of the novel concepts of the present invention, but it is understood that this application is to be limited only by the scope of the appended claims.

The invention is hereby claimed as follows:

1. In combination with a disc-shaped orthodontic attachment having a protruding portion, a holder for holding the attachment during the securing of same to a tooth band, said holder comprising a pair of integrally connected panels folded together along a common edge and sandwiching therebetween the holder, an opening in said panels through the common edge having the attachment aligned therewith exposing nearly all of the attachment with the protruding portion centered through the opening at one panel so that the attachment may be placed upon a tooth band and held in place by engaging the holder during securing of same to the tooth band, means for holding the free edges of the panels together, and said opening being sized slightly under the size of the attachment such that the attachment cannot pass therethrough unless forced to do so which enlarges the opening.

2. The combination defined in claim 1, wherein the holder is constructed of a relatively stiff material such that the attachment cannot move freely through the opening.

3. The combination defined in claim 2, wherein the material is transparent, and wherein the panels include a plurality of openings for a plurality of attachments.

4. The combination as defined in claim 3, wherein the means for holding the free edges of the panels together includes a locking flap on one of the panels overlying the free edge of the other panel.

5. The combination as defined in claim 3, wherein the means for holding the free edges of the panels together includes a layer of adhesive on one of the panels at the free edge.

6. The combination as defined in claim 3, wherein the material is heat-sealable, and the means holding the free edges of the panels together includes a heat-sealed joint.

* * * * *